United States Patent [19]

Jahr et al.

[11] Patent Number: 4,975,430
[45] Date of Patent: Dec. 4, 1990

[54] CNQX AND ITS ANALOGS AS THERAPEUTICS FOR DEGENERATIVE NEURAL DISEASES

[75] Inventors: Craig E. Jahr; Robin Lester; Eckard Weber, all of Portland, Oreg.

[73] Assignee: The State of Oregon Acting by and Through The State Board of Education on Behalf of The Oregon Health Sciences University, Portland, Oreg.

[21] Appl. No.: 367,993

[22] Filed: Jun. 16, 1989

[51] Int. Cl.⁵ .......................................... A61K 31/495
[52] U.S. Cl. .................................................. 514/255
[58] Field of Search ........................................ 514/255

[56] References Cited

U.S. PATENT DOCUMENTS 4,812,458 3/1989 Honore et al. ...................... 514/249

OTHER PUBLICATIONS

Honore et al., *Science* (1986) 241:701-703.
Blake et al., *Neuro Sci. Let.* (1988) 89:182-186.
Fletcher *Brit. J. Pharmacol.* (1988) pp. 586-587.
Drejer et al., *Neuro Sci. Let.* (1988) 87:104-108.
Birch et al., *Eur. J. Pharmacol.* (1988) 151:313-315.
Kemp et al., *Proc. Natl. Acad. Sci. U.S.A.* (1988) 85:6347-6350.
Kestler et al., *Soc. Neuro. Sci. Abstr.* (Abstr. (1987) 13:760.
Lester et al., *Mol. Pharmacol.* (1989) pp. 1-6.
Chem. Abst. 109:14034u (1988).

*Primary Examiner*—Stanley J. Friedman
*Attorney, Agent, or Firm*—Irell & Manella

[57] ABSTRACT

Compounds of the formula

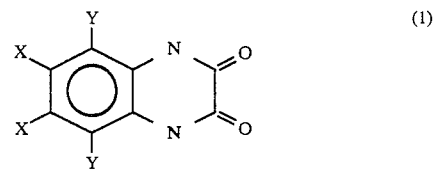

wherein each X is independently nitro or cyano and wherein each Y is independently H, lower alkyl (1-4C), lower alkoxy (-4C), or CF₃ have been shown to be successful antagonists of NMDA receptors. Accordingly, these compounds are useful in the treatment of neuronal conditions associated with stimulation of the NMDA receptor.

5 Claims, 4 Drawing Sheets

CNQX AND ITS ANALOGS AS THERAPEUTICS FOR DEGENERATIVE NEURAL DISEASES

TECHNICAL FIELD

The invention relates to therapeutics useful in neurologic diseases. More particularly, it concerns the use of nitroquinoxaline-2,3-diones in the treatment of degenerative diseases of the nervous system.

BACKGROUND ART

It has been recognized for some time that the transmission of signals through the nervous system is mediated by a variety of neurotransmitters, each of which has a complementary receptor in the neuron. A substantial number of classes of neurotransmitters and their receptors have been recognized.

One important excitatory neurotransmitter is the amino acid L-glutamate. Receptors which respond to this amino acid have been divided into NMDA and non-NMDA receptors; NMDA, N-methyl-D-aspartate, is an additional neurotransmitter which has its own class of receptors. NMDA receptors are known to be regulated by a glycine binding site which regulates the ability of the neuron to respond to NMDA; glycine in nanomolar concentrations potentiates the NMDA receptor-induced current in a strychnine insensitive manner. Substances which behave as agonists or antagonists with respect to NMDA receptors can therefore interact either with the receptor site for NMDA or the receptor site for glycine or both. Antagonists for these NMDA receptors ameliorate the effects of L-glutamine and are therefore beneficial in the treatment of degenerative neural diseases which are characterized by abnormal neuronal stimulation, such as epilepsy, brain degeneration due to stroke or heart attack, Alzheimer's disease, Lou Gehrig's's disease, and Huntington's disease.

The compound 6-cyano-7-nitroquinoxaline 2,3-dione (CNQX) and the related compound 6,7-dinitro-quinoxaline-2,3-dione (DNQX) are known to depress the excitation of spinal cord neurons which are induced by the stimulation of non-NMDA receptors. See U.S. Pat. No. 4,812,458. However, it was also reported that these compounds had little or no effect on responses produced by NMDA (Honore, T. S. et al., Science (1986) 241:701–703; Blake, J. F. et al., Neuro Sci Let (1988) 89:182–186; Fletcher, E. J., Brit J Pharmacol (1988) 586–587; Dryer, J. et al., Neuro Sci Let (1988) 87:104–108).

Although others have shown that CNQX and DNQX do not interfere with the action of NMDA itself, it has been shown that DNQX produces a shift to the right in the NMDA concentration response curve and a decrease in maximal response at high antagonist concentrations (Birch, P. J. et al, Eur J Pharmacol (1988) 151:313–315. A similar result was noted when DNQX was replaced in these assays by compounds known to displace labeled glycine from the strychnine insensitive binding site (Kemp, J. A. et al., Proc Natl Acad Sci USA (1988) 85:6347–6350; Kestler, M. et al., Soc Neuro Sci Abst (1987) 13:760. As stated above, it is known that binding glycine to a regulatory site potentiates the response of these receptors to NMDA.

It has now been found that despite its apparent inability to interfere with NMDA stimulation, CNQX, DNQX and their analogs behave as antagonists with respect to stimulation to the NMDA receptor.

DISCLOSURE OF THE INVENTION

The invention provides useful compounds for therapeutic prevention and treatment of neuronal diseases which are mediated through stimulation of the NMDA receptor. Such diseases include Alzheimer's disease, Lou Gehrig's disease, Huntington's disease, epilepsy, and brain damage due to stroke.

Thus, in one aspect, the invention is directed to a method to prevent, ameliorate, or otherwise treat these diseases by administration of effective amounts of CNQX or DNQX or their analogs. In another aspect, the invention is directed to pharmaceutical compositions in unit dosage form which are useful in this method.

MODES OF CARRYING OUT THE INVENTION

Figure 1:
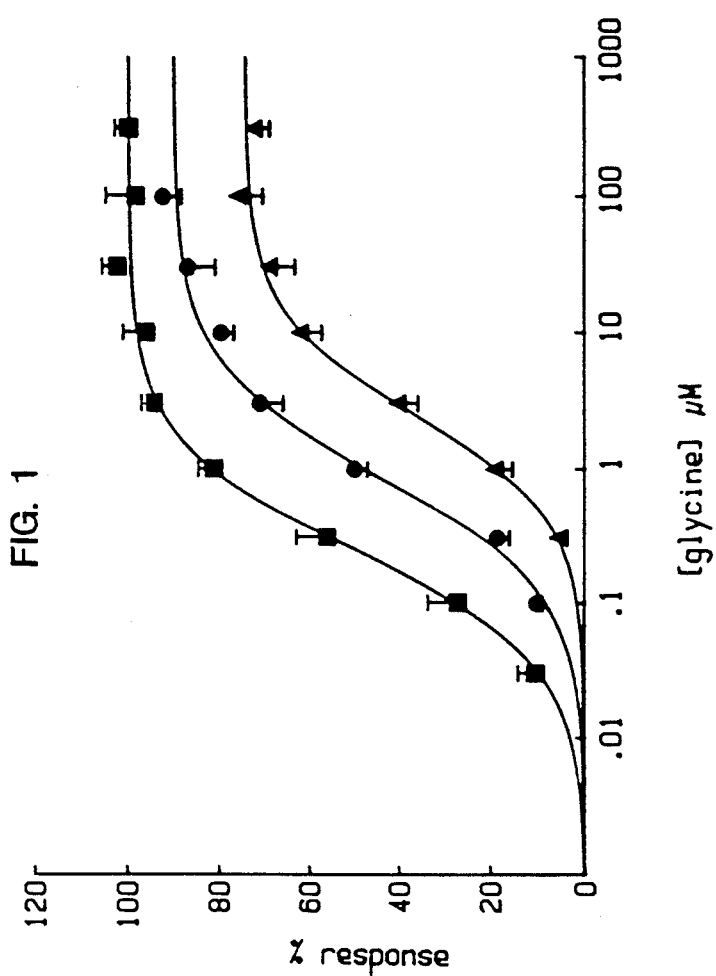
FIG. 1 shows the effect of two concentrations of CNQX on the response curve for the NMDA receptor in the presence of various concentrations of glycine.

As used herein, CNQX and DNQX and their analogs refers to compounds of the formula:

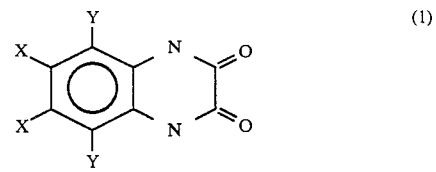

each X is independently nitro or cyano and each Y is independently a non-interfering substituent selected form the group consisting of H, lower alkyl(1–4C), $CF_3$, and lower alkoxy(1–4C). Lower alkyl refers to a straight or branched chain hydrocarbyl substituent such as methyl, ethyl, isopropyl, or isobutyl. Lower alkoxy is a substituent of the formula -OR wherein R is lower alkyl as above defined. Particularly preferred are embodiments of the compound of formula (1) wherein both Y are H and both X are nitro or wherein both Y are H and one X is nitro and the other cyano, i.e., DNQX and CNQX respectively. Other preferred embodiments include those wherein both Y are methyl or wherein one Y is methyl and the other Y is H, and wherein X is as described above.

The compounds of formula (1) are useful in the treatment of conditions of the nervous system which are mediated by the NMDA receptor. It is understood currently that among diseases affected by the NMDA receptor simulation are epilepsy, Alzheimer's, Lou Gehrig's disease, Huntington's disease and brain degeneration caused by stroke or trauma. However, any disease currently understood to be a function of NMDA receptor stimulation or subsequently shown to be thus mediated is a suitable substrate condition for the administration of the compound of formula (1).

In the method of the invention, the compounds of formula (1) are administered to subjects showing the above-mentioned indications in suitable pharmaceutical compositions and by routes of administration ordinarily used for simple compounds which target the nervous system. A preferred mode of administration is by injection, either intravenous, intramuscular, or subcutaneous, particularly subcutaneous injection in areas, such as immediately behind the ear, wherein the neuronal system can be reasonably directly addressed. Other routes of administration are also possible, such as application across membranes, e.g., transmucosal administration or transdermal administration. Oral administration can also be used.

The formulation and dosage range depend on the route of administration, the condition of the subject, and the judgment of the physician, and can be optimized using standard procedures for designing dosage. For administration systemically through injection, a suitable dose is in the range of 0.1 ug/kg-1 mg/kg. However, smaller and larger doses may be required depending on the specific situation.

For administration by injection, the compounds of formula (1) are administered in solution or suspension in suitable excipient, such as Hank s solution, Ringer's solution, physiological buffer in general, or water for injection. For transmucosal administration, suitable excipients include membrane penetrants such as bile salts and the fusidates. The materials for transmucosal administration can be formulated as sprays or suppositories. For oral administration, the compounds of formula (1) are administered in capsule, tablet, or liquid form. Suitable methods for formulation and administration are understood in the art, and an encyclopedia of such approaches can be found in *Remington's Pharmaceutical Sciences*, Mack Publishing Company, Easton, Pa., (latest edition).

The compounds of formula (1) are generally available commercially.

The following examples are intended to illustrate but not to limit the invention.

PREPARATION A

Preparation of NMDA Receptor Containing Substrate

In a modification of the method of Jahr, C. E. et al., *Nature* (1987) 325:522-525, hippocampi were dissected from brains of 1-3 day old Long-Evans rats, chopped into blocks of less than 1 mm$^3$ and transferred into a papain solution (20 units/ml) in which they were incubated with constant agitation for 30 min at 37° C. The tissue was dissociated into a single cell suspension in complete growth medium (minimum essential medium with Earle's salts, 20 mM glucose, 50 units/ml penicillin/streptomycin, 5% host inactivated fetal calf serum and 1:1000 serum extender) that contains 2.5 mg/ml bovine serum albumin and 2.5 mg/ml trypsin inhibitor using a fire-polished Pasteur pipette.

The suspension was plated onto glass cover slips coated with poly D-lysine (0.1 mg/ml) and collagen (0.5 mg/ml). One-half of the growth medium was exchanged every 2-3 days, and when the astrocytes were 80% confluent (4-7 days) 5 mM cytosine arabinoside was added to prevent further division of glial cells. After 7 days in culture, neurons were killed by incubation for 30 min in a balanced salt solution containing 100 mM glutamate. This provided a confluent non-neuronal background feeder layer on which newly dissociated neurons could be plated at low density, thereby minimizing synaptic contacts and reducing transmitter release resistant to tetrodotoxin (TTX).

Neurons maintained in culture for 1-3 weeks were dissociated and plated on the confluent layer for electrophysiology experiments.

PREPARATION B

Preparation of Neural Membrane

The frontal cortex from frozen guinea pig brains was homogenized in 10 volumes (w/v) of 0.32M sucrose. The homogenate was centrifuged (1000 x g, 10 min, 4° C.). The supernatant was recovered and centrifuged at 20,000 g, 20 min, 4° C. The resulting pellet was resuspended to a protein concentration of 2.5 mg/ml using the method of Bradford, M. A., *Anal Biochem* (1976) 72:248-254 and stored at 20 ml aliquots at −70° C. for at least 45 hours before use.

For assay, the crude membranes were thawed the same day and resuspended in assay buffer (50 mM tris/citrate, pH 7.2). The membranes were then centrifuged at 20,000 x g for 20 min and resuspended in assay buffer to a protein concentration of 2.5 mg/ml. The preparation was treated with 0.1% Triton X-100 and 0.1% EDTA on ice for 20 min to remove endogenous ligands. The suspension was centrifuged for 20 min at 20,000 x g to recover the membranes. The membranes were washed before the assay an additional 3 times with assay buffer.

EXAMPLE 1

Effect of CNQX on Glycine Potentiation

NMDA receptor-mediated currents were measured using tight seal whole cell patch recordings at room temperature (25° C.) using the dissociated neurons prepared as described in Preparation A. The recordings were made using an Axoclamp to an amplifier in discontinuous voltage clamp mode (switching frequency 10-15 Hz) or an Axopatch 1B patch clamp amplifier. The currents were low pass filtered (300-1000 Hz) and recorded on a Gould chart recorder or digitally sampled at 50-200 Hz. The cells were voltage-clamped at −60 mV.

In the assay, patch pipettes were filled with an intracellular solution containing 160 mM calcium gluconate, 10 mM CsCl, 1 mM EGTA, 1.5 mM Mg-ATP, 5 mM HEPES, adjusted to pH 7.4 with CsOH. During recording, the cells were continuously superfused (2-5 ml/min) with an external solution containing 165 mM NaCl, 3 mM KCl, 2 mM CaCl$_2$ and 5 mM HEPES adjusted to pH 7.4 with NaOH. A 0.5 uM solution of TTX was added to reduce spike-triggered synaptic activity, and 100 uM picrotoxin in 1 μM strychnine were added to the external medium. Solutions containing test materials were prepared in the external medium and applied close (less than 10 um) to the cell under study through multi-barreled perfusion pipettes which enable rapid switching between solutions as described by Johnson, J. W. et al., *Nature* (1987) 325:529-531. One of the barrels always contained external buffer alone which provided rapid washout after application of the test substance. Solution changes were complete in less than 200-250 msec as judged by the time to peak response to a non-desensitizing concentration of NMDA/glycine.

NMDA receptor currents were measured in the presence of varying concentrations of glycine in the presence and absence of CNQX. Solutions containing NMDA and the designated glycine concentration were added with and without CNQX as described above. The effect of CNQX on NMDA receptor mediated currents are shown in FIG. 1. In the experiment there shown, the neurons were voltage-clamped as described at 60 mv in each cell, 3-5 separate points were obtained with reference to a standard and the data were fitted to a logistic equation by the least squares method. The error bars indicate the standard deviation.

In FIG. 1, the solid squares show the effect of varying concentration of glycine on the receptor-mediated currents stimulated by NMDA in the absence of CNQX. The solid circles show this effect in the presence of 10 uM CNQX; the solid triangles in the presence of 30 uM CNQX. As the results in FIG. 1 indicate, higher concentrations of glycine are necessary to obtain potentiation of the receptor-mediated currents in the presence of higher concentrations of CNQX, and complete potentiation is not achieved in the presence of this compound.

EXAMPLE 2

Reversal of CNQX antagonist activity by Glycine

Figure 2A:
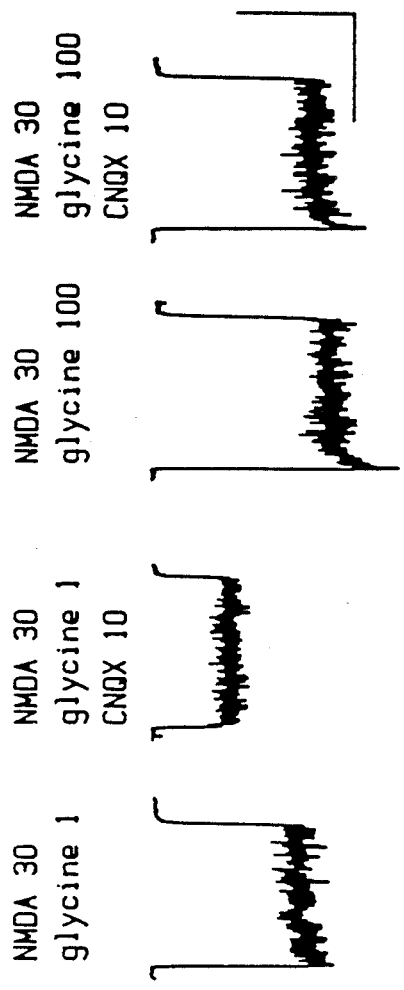
FIG. 2 shows the effect of increased glycine concentration and increased NMDA concentration on CNQX antagonism.
Figure 2B:
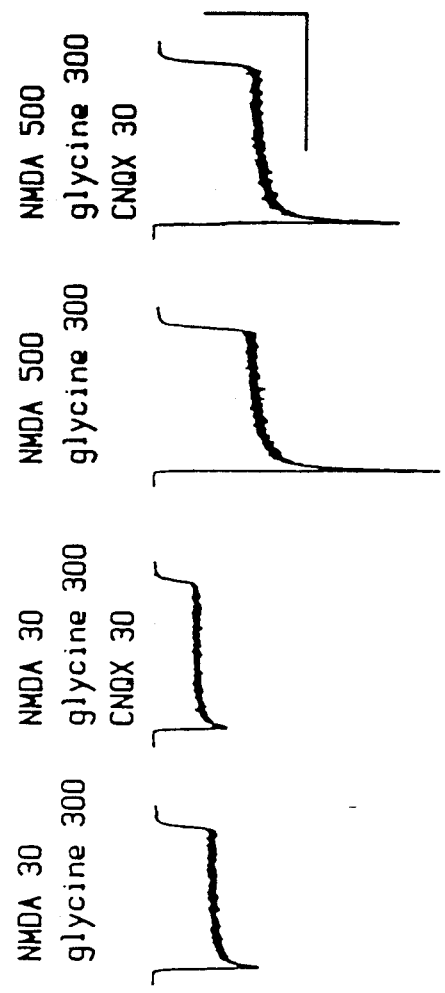

Receptor-mediated currents were measured as in Example 1 in the presence of 30 uM NMDA. In the presence of 1 uM glycine, as shown in FIG. 2A, the presence of 10 10 uM CNQX suppresses the response. However, when the glycine concentration is elevated to 100 uM, the addition of 10 uM CNQX has substantially no effect. The relatively low suppression shown by 30 uM CNQX in the presence of 30 uM NMDA and 200 uM glycine can be reversed as shown in FIG. 2B by enhancing the concentration of NMDA to 500 uM. Thus, the effect of CNQX antagonism can be reversed by very high concentrations of either NMDA or glycine.

The effects of CNQX as described in this example and Example 1 were not dependent on membrane potential as currents recorded at +40 mv and −40 mV were substantially identical.

In an additional control experiment, the effect of CNQX on stimulation of the non-NMDA receptor for kainate, known to be antagonized by CNQX, could not be reversed by glycine. In this experiment, the neuron preparation described in Preparation A was treated with 20 uM kainate and 1 uM glycine in the presence and absence of 10 uM CNQX. As expected, the CNQX resulted in a complete suppression of the kainate-mediated current. A glycine concentration of 1000 uM had no effect on this suppression.

EXAMPLE 3

Effect of CNQX on Glycine Binding

Washed membranes prepared as described in Preparation B (150-200 ug) were incubated with 4 nM 3-H-glycine (43.5 Ci/mmol) and unlabeled test substance or buffer in a final volume of 0.2 ml. After incubation on ice for 30 min, the reaction was terminated by rapid filtration at 4° C. using no. 32 glass filters (Schleicher and Schuell) pretreated with 0.05% polyethyleneamine. The filters were washed with 5 ml cold assay buffer and radioactivity was measured by liquid scintillation counting. Nonspecific binding measured in the presence of 1 mM glycine varied between 5-10% of the total 3H glycine binding. Saturation data were evaluated by Scatchard analysis using EBDA and LIGAND data analysis programs.

Figure 3:
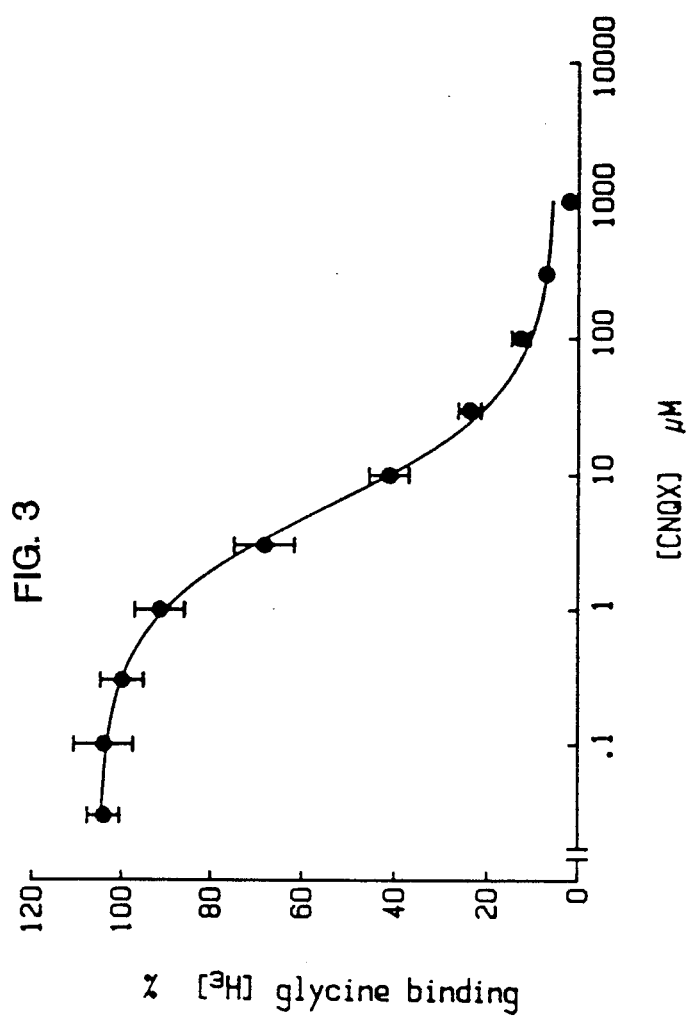
FIG. 3 shows the inhibition of binding of labeled glycine to membranes in the presence of increasing concentrations of CNQX.
Figure 4:
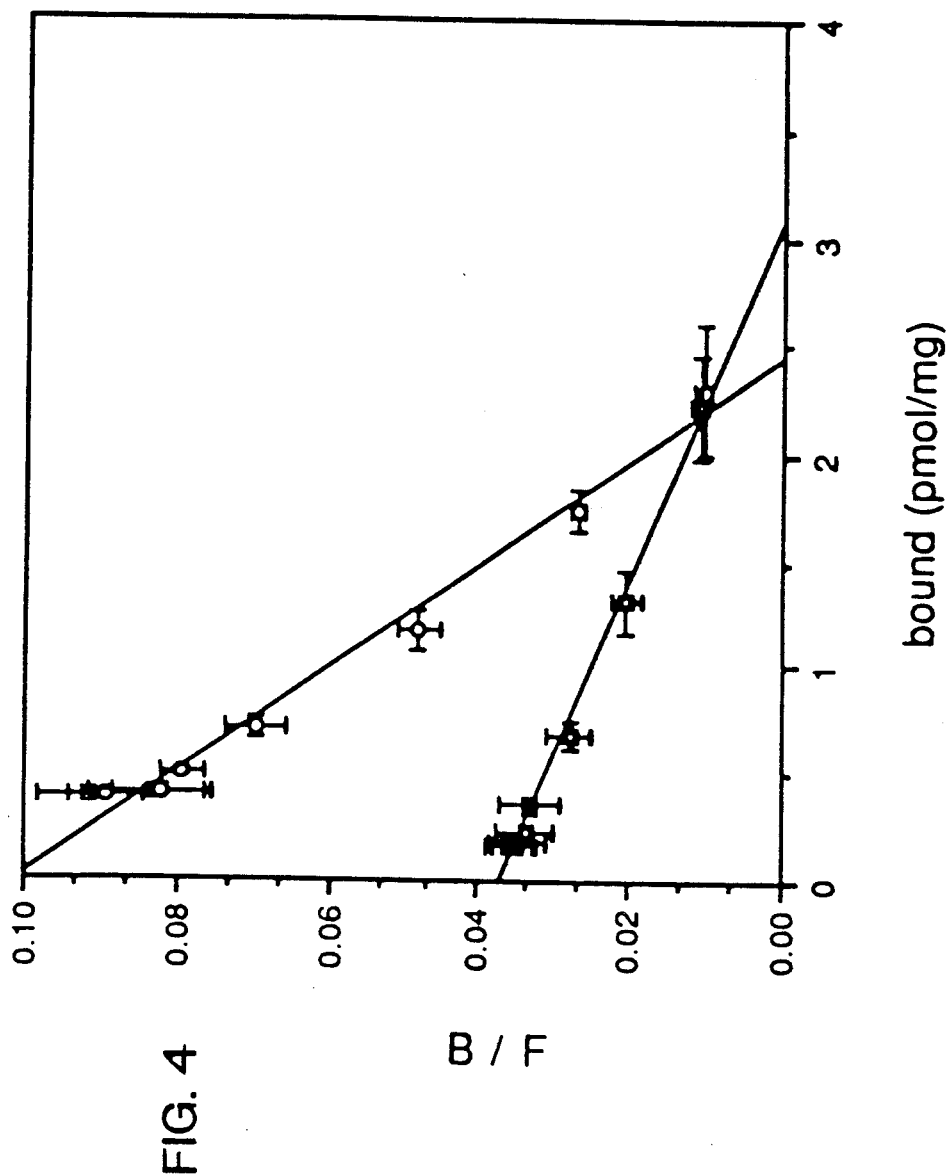
FIG. 4 shows a Scatchard plot of labeled glycine binding in the presence and absence of CNQX.

The effect of CNQX on the binding of labeled glycine is shown in FIG. 3. As shown, CNQX has an $IC_{50}$ value of 5.7 uM for displacement of glycine. A Scatchard plot of these data is shown in FIG. 4.

EXAMPLE 4

Injectable CNQX Composition

An injectable preparation buffered to pH 7 is prepared having the following composition:

| Ingredients | |
| --- | --- |
| CNQX | 0.2 g |
| $KH_2PO_4$ buffer (0.4 M solution) | 2 ml |
| KOH (1 N) | q.s. to pH 7 |
| Water (distilled, sterile) | q.s. to 20 ml |

EXAMPLE 5

Composition for Transmucosal Administration

A pharmaceutical preparation for transmucosal delivery has the following composition:

| Ingredients | |
| --- | --- |
| CNQX | 0.1 g |
| phosphate buffer (0.2 M, pH 7.4) | 4 ml |
| bile salts | 0.1 g |
| water (distilled, sterile) | q.s. to 20 ml |

EXAMPLE 6

Composition for Oral Administration

A pharmaceutical preparation for oral delivery has the following composition:

| Ingredients | |
| --- | --- |
| DNQX | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| flavoring | 0.035 ml |
| water (distilled) | q.s. to 100 ml |

What is claimed is:

1. A method to treat neuronal diseases mediated by stimulation of the NMOA receptor which method comprises administering to a subject in need of such treatment an effective amount of a compound of the formula

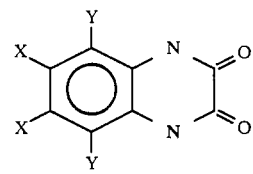

(1)

wherein each X is independently nitro or cyano and wherein each Y is independently H, lower alkyl (1-4C), lower alkoxy (1-4C), or $CF_3$, or a pharmaceutical composition thereof in an amount effective to ameliorate said condition.

2. The method of claim 1 wherein both Y are H, and both X are nitro or one X is nitro and the other is cyano.

3. The method of claim 2 wherein both X are nitro.

4. The method of claim 2 wherein one X is nitro and the other is cyano.

5. The method of claim 1 wherein both Y are methyl or wherein 1 Y is methyl and the other is H, and wherein both X are nitro or one X is nitro and the other is cyano.

* * * * *